United States Patent [19]

Felthouse

[11] Patent Number: 4,959,494
[45] Date of Patent: Sep. 25, 1990

[54] OXIDATION OF ORGANIC COMPOUNDS WITH PYROCHLORE CATALYSTS

[75] Inventor: Timothy R. Felthouse, St. Louis, Mo.

[73] Assignee: Monsanto Company, St. Louis, Mo.

[21] Appl. No.: 70,091

[22] Filed: Jul. 6, 1987

Related U.S. Application Data

[63] Continuation of Ser. No. 807,010, Dec. 11, 1985, abandoned.

[51] Int. Cl.$^5$ .............................................. C07C 51/21
[52] U.S. Cl. .................................. 562/515; 544/170; 558/123; 562/400; 562/408; 562/421; 562/527; 562/528; 562/531; 562/538; 562/537; 562/544; 562/545; 562/546; 562/542; 568/27; 568/320; 568/360; 568/402; 568/471
[58] Field of Search ............... 562/542, 531, 537, 538, 562/527, 545, 546, 544, 515, 528, 534, 543, 535, 421, 408, 400, 536; 568/401, 8, 402, 471, 27, 28, 320, 360, 402, 471; 564/298

[56] References Cited
U.S. PATENT DOCUMENTS
4,129,525 12/1978 Horowitz et al. .................. 502/326

Primary Examiner—Werren B. Lone
Attorney, Agent, or Firm—Charles E. Smith; Linda L. Lewis; James W. Williams, Jr.

[57] ABSTRACT

A method for oxidizing organic compounds by contacting organic compounds with molecular oxygen in the presence of a noble metal pyrochlore having the formula:

$$A_{2+x}B_{2-x}O_{7-y}$$

wherein A is a pyrochlore structure metal cation, and B is one or more of Ru, Rh, Ir, Os, and Pt; x and y are greater than or equal to 0 and less than or equal to 1.0, at a temperature up to about 200° C.

14 Claims, 3 Drawing Sheets 220   200   180   160   140   120   100   80   60   40   20 PPM0

OXIDATION OF ORGANIC COMPOUNDS WITH PYROCHLORE CATALYSTS

This is a continuation of application Ser. No. 807,010, filed Dec. 11, 1986, now abandoned The present invention relates to a method of selectively oxidizing organic compounds to desired products, and more particularly to a method of oxidizing alcohols, olefins and carbonyl compounds to carbonyl compounds and carboxyl or carboxylate compounds by contact with pyrochlore compounds and molecular oxygen.

BACKGROUND OF THE INVENTION

Metal oxides of the pyrochlore structure have been known heretofore and are generally described as of the general composition $A_{2+x}B_{2-x}O_{7-y}$ wherein A is Pb, Bi, Tl, Sn or any combination thereof, and B is one or more of Ru, Rh, Ir, Os, and Pt, and wherein x and y are each equal to or greater than zero and equal to or less than 1. It has been taught in U.S. Pat. No. 4,129,525 that the described pyrochlore compounds can be fabricated into high surface area materials which can be used as electrodes in the evolution or reduction of oxygen in alkaline solutions. It has further been taught in U.S. Pat. No. 4,434,031 that the described high surface area pyrochlore compounds, with U.S. Pat. No. 4,129,525 and related patents being referenced, can be used as anodes in electrolytic cells in a method of electrocatalytically oxidizing an oxidizable organic compound. The method is described as useful for electrocatalytically generating carboxylates from primary alcohols, olefins, glycols, keto alcohols, diketones, keto acids and hydroxy acids, and certain cleavage reactions and conversion of secondary alcohols to ketones are also described. Certain defect pyrochlores have been proposed as a catalyst support with gas-phase oxidation of hydrocarbons or CO to $CO_2$ being attributed to platinum on the surface; see Goodenough et al, *J. Solid State Chem.* 44, 108 (1982). The pyrochlores were employed as powdered crystals rather than as high surface area materials.

SUMMARY OF THE INVENTION

It has now been found that pyrochlores can be employed as oxidation catalysts to oxidize selectively organic compounds to desired compounds, employing molecular oxygen as an oxidizing agent. The oxidation can be effected in liquid media, and appears to involve hydroxide ion in the charge transfer and incorporation of oxygen into the organic compounds. Aqueous media are particularly suitable for the reaction, and strongly alkaline conditions have been found very effective. The pyrochlores are used in the presence of oxygen under conditions such that the oxygen supplied to the pyrochlore is generally at least sufficient to match the utilization of the activated oxygen by the organic substrate. Whether the oxygen is actually incorporated in the pyrochlore or not, it is apparent hat there is an uptake of oxygen to result in oxidation of the organic substrate. It is advantageous that the oxidations can be effected at relatively mild temperatures, such as temperatures ranging from 0° to 200° C., or more preferably, about 20° to about 100° C. Oxygen will generally be present in amount sufficient for a desired reaction rate or as needed to maintain a reaction, with mildly elevated pressures such as about 5 to about 100 psi (34.5 to 689.5 kPa) gauge being preferred and contributing to the effectiveness of the oxidation; however, oxygen can suitably be provided at other pressures, such as from atmospheric pressure up to 1000 psi gauge or higher. It is also very advantageous in the present invention to employ the pyrochlore in a high surface area form, such as in form having surface area of at least 15 meters$^{2/}$-gram, and usually in form of much higher surface area. In particular aspects, the invention involves using the oxidation with pyrochlore catalysts as described to effect conversions of particular functional groups in organic compounds to other functional groups, while generally retaining the rest of the compound in its original form. Thus some reactions involve the conversion of alcohol or aldehyde groups to carboxylic acid groups. Others involve cleavage reactions as well as functional group conversions, as in the case of secondary alcohols, olefins and alkynes, the compounds may be cleaved and oxidized to two separate carboxylic acids, with production of ketone intermediates being feasible with the secondary alcohols and alkynes. Cobalt catalysts have been used in the past for similar reactions, but under anhydrous conditions and generally at higher temperatures. It is advantagous that the present process is effective at mild conditions in liquid phase, especially in using aqueous media for water soluble substrates. It is of special interest that the present oxidation process is suitable for effective cleavage and hydroxyl oxidation reactions with various carbohydrates to produce various polycarboxylate compounds, as prior procedures for effecting such reactions have generally required expensive reoxidants for the oxidizing agent, or have been poorly suited for use in liquid media at low temperatures. Pressurized vessels such as autoclaves are particularly suitable for the processes of the present invention.

BRIEF DESCRIPTION OF THE DRAWINGS

The drawings of this application include Figures which are NMR spectra of compounds before, and after, oxidation in accord with procedures of the present invention.

DETAILED DESCRIPTION

Figure 1:
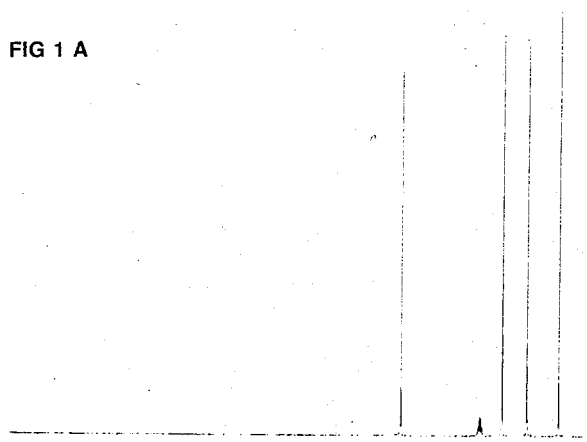
FIG. 1 illustrates NMR spectra of solutions of 2-butanol and various oxidation products derived from it.
Figure 1:
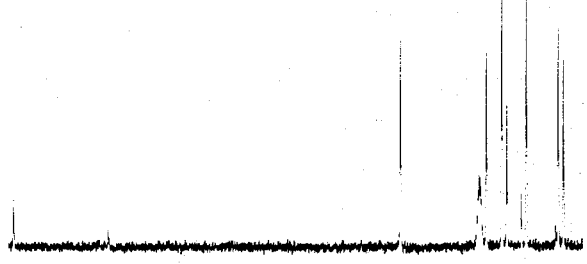
Figure 1:
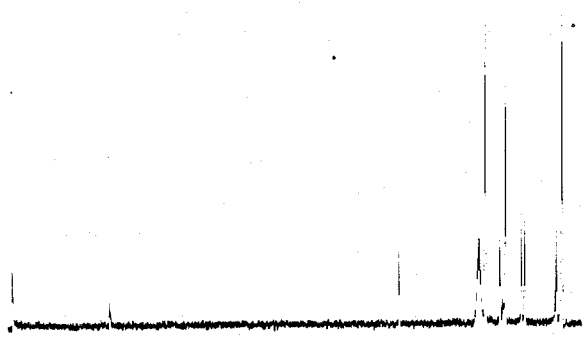
Figure 1:
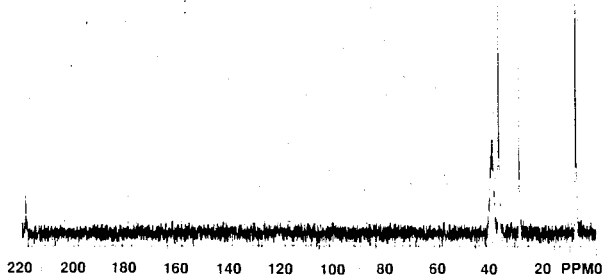

The present invention makes possible a convenient, low temperature oxidation of organic substrates in liquid media to useful products, using oxygen as an oxidizing agent. The process utilizes a pyrochlore oxide catalyst system. The pyrochlores utilized herein generally conform to the structure:

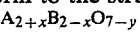

where:
  A is Pb, Bi, Tl, Sn or any combination thereof
  B is Ru, Rh, Ir, Os, Pt, or combinations thereof; and
  each of x and y is greater than or equal to zero and less than or equal to 1. where:
    and each of x and y is greater than or equal to zero and less than or equal to 1.

The pyrochlores utilized herein in general display the pyrochlore crystal structure; see *Structural Inorganic Chemistry*, Fourth Ed., by A. F. Wells, Clarendon Press, Oxford, 1975. The structure can be represented, $A_{2+x}B_{2-x}O_6O'$ wherein A and B are metal cations.

The oxides typically have a face-centered cubic structure having a unit cell dimension of about 10Å. The cations are octahedrally coordinated by oxygen anions. The structural framework is formed by a three dimensional array of these corner shared octahedra, each sharing corners with six others. This framework has the composition $B_2O_6$. As Wells describes, this framework of octahedra is "based on the diamond net, having large holes which contain the O' and two A atoms, which themselves form a cuprite-like net $A_2O'$ interpenetrating the octahedral framework". The octahedra are actually arranged in tetrahedral clusters. These clusters of octahedra are then tetrahedrally arranged so as to form the large holes in the structure described by Wells. Each of these large holes may also be defined by four tetrahedrally arranged puckered, hexagonal rings which are formed by the corner shared octahedra. The A cations reside in the center of these puckered hexagonal rings and are coordinated by the six O anions which define the rings plus two more O' cations at a slightly different distance. These O' anions reside at the center of the large holes in the octahedral framework. It is the O' anions which may be partially or totally absent, leading to the general pyrochlore oxide formula $A_{2+x}B_{2-x}O_{7-y}$ where x can vary from 0 to 1 and where $0 < y < 1$. Thus, the compounds made by the method of the present invention are referred to as pyrochlore compounds, albeit they are not stoichiometric pyrochlores, but rather are lead-rich, bismuth-rich compounds, or rich in the A element of the formulas as above. In some cases the pyrochlores exhibit an expanded lattice structure from the amount of excess lead, bismuth, or A-type element in the crystalline structure. Pyrochlore type structures and methods of preparation are further described in Bouchard, U.S. Pat. No. 3,583,931, and Horowitz et al, U.S. Pat. No. 4,129,525, the disclosures of which are incorporated herein by reference.

While the above formula $A_{2+x}B_{2-x}O_{7-y}$ provides the fundamental composition of the pyrochlores used herein, it is also possible to have other components substituted in such formula or present as contaminants, and still have pyrochlores effective for the present invention. Thus, various other metals can be present in minor, or possibly up to equimolar amount with the A metal, such as yttrium, silver, cadmium, indium, thalium and rare earths numbers 57 to 71 inclusive; and minor amounts of titanium, chromium and antimony can be substituted for the B metal. For example, it is feasible to use pyrochlores as described in the aforesaid Patent No. 3,583,931, represented by the formula, $(M_xBi_{2-x})(M_y'M''_{2-y})O_{7-z}$, in which M is at least one of the group consisting of yttrium, silver, cadmium, indium, thalium and rare earth metals of atomic number 57–71, inclusive;

M' is at least one of platinum, titanium, chromium, rhodium, and antimony;

M'' is at least one of ruthenium and iridium;

x is a number in the range 0 to 1;

y is a number in the range 0 to about 0.5, with the proviso that y is a number in the range 0 to 1 when M' is rhodium or more than one of platinum, titanium, chromium, rhodium and antimony; and z is a number in the range 0 to 1, being at least equal to about x/2 when M is divalent lead or cadmium.

It is also suitable to use pyrochlores as disclosed in U S. Pat. No. 4,420,422 as represented by the formula:

$Bi_{2-x}M_xB_2O_{7-z}$ wherein

M is selected from the group consisting of cadmium, copper, lead, indium, gadolinium, silver and mixtures thereof;

B is selected from the group consisting of ruthenium, iridum and mixtures thereof, x is from 0 to 0.5 and z is 0 to 1.

Pyrochlore oxides are used in the present process as catalysts for reactions involving the oxidation of organic compounds by oxygen. One aspect of the effectiveness of pyrochlores for such reactions is the ability of the catalyst to reduce oxygen. A further patent of Horowitz et al, U.S. Pat. No. 4,146,458, describes a class of pyrochlores as suitable for use in oxygen electrodes to reduce or generate oxygen, in electrochemical devices, and such pyrochlores are suitable for use in the present invention, being of the formula A wherein A is any of the known pyrochlore structure cations and B is a pyrochlore structure metal cation at least a major portion of which is selected from the group consisting of one or more of Ru, Rh, Ir, Os, Pt, Ru—Pb mixtures and Ir—Pb mixtures and wherein $0 \leq y \leq 1.0$. A in the cited formula is desirably selected in at least a major proportion from one or more of Pb, Bi, and Tl. A preferred group in the said patent is of formula Pb wherein M is selected from the group consisting of Ru and Ir, and $0 = X = 1.0$ and $0 = y = 1.0$; such preferred group of pyrochlores will also be very suitable for the present process. The various specific pyrochlore compounds disclosed in the patent, which is incorporated herein by reference, can also be used in the present invention.

Ruthenium pyrochlores appear to be very useful for oxidations in the present process, particularly such pyrochlores which also contain lead or bismuth, such as represented by $Pb_{2+x}Ru_{2-x}O_{7-y}$, $Bi_{2+x}Ru_{2-x}O_{7-y}$ and $(Pb-Bi)_{2+x}Ru_{2-x}O_{7-y}$ where each of x and y can vary from zero to 1.

The present process involves the take-up of oxygen and the oxidation of organic compounds, so the reduction of oxygen is involved and the pyrochlore oxide must be effective in mediating such reduction. Effectiveness for oxygen reduction can be determined electrocatalytically by employing the pyrochlore as an electrode in a potentiostated half-cell, such as that used in the aforesaid U.S. Pat. No. 4,129,525, where a performance curve was obtained for electrocatalytic reduction of oxygen at a pyrochlore electrode in 3N KOH at 75° C., with the conclusion that the pyrochlore was superior to a supported platinum electrocatalyst in the tested environment. Under such test conditions, the better pyrochlores for use herein will exhibit significant potentials, and often better than 0.5 millivolt vs. the reference hydrogen electrode, at a current density of 100 milliamperes/cm$^2$.

In the referred-to U.S. Pat. No. 4,434,031, it is shown that a pyrochlore anode can undergo oxidative change, i.e. charging, as a function of potential in alkaline solution, and then reduction by propylene. In the present process it is not necessary to impose any electrical potential, but rather the charging of the electrode is achieved by the effect of the oxygen in the medium upon the pyrochlore material. Thus when pyrochlore catalyst material is placed in an alkaline medium under oxygen pressure, with an oxidizable organic compound, there is a definite uptake of oxygen which can be measured by pressure or oxygen supply instruments. While both the oxygen and organic compound are generally in contact with the pyrochlore at the same time in the present invention, and the pyrochlore maintained in a "charged state, the pyrochlore could for demonstration purposes first be "charged" by contact with oxygen in an alkaline medium, and then reduced by contact with an oxidizable organic compound. Thus the pyrochlore materials used are characterized by ability to take up oxygen when molecular oxygen is provided in alkaline media. If desired, the ability of particular pyrochlores to take up oxygen can be measured by means such as employed in the stated U.S. Pat. No. 4,434,031, the disclosure of which is incorporated herein by reference. In the formula for pyrochlores, the amount of oxygen is generally designated by some non-integral subscript showing it is present in a non-stoichiometric amount, such as 6.5 or some other value between 6 and 7. In the use of the pyrochlores in the present invention, as it is oxidized and reduced, the actual changes in the oxygen content may be small fractional changes, with little tendency to reach an oxygen content of 7 or to decline to an oxygen content of 6.

The pyrochlore oxides for use herein can be prepared by any of the procedures known to the art. However, there is a preference for procedures which give high surface area materials, such as those with surface areas greater than 15 meters$^2$/gram, and preferably surface areas in the range of 50 to 200 meters$^2$/gram or higher. The low temperature synthesis in alkali hydroxide solutions is particularly suitable, being taught in the aforesaid U.S. Pat. Nos. 4,129,525 and 4,440,670, and particularly the procedures conducted in the presence of oxygen. The precipitation-calcination procedure taught in the aforesaid U.S. Pat. No. 4,410,422 can also be employed, as can procedures involving evaporative decomposition of solids, or methods where a support, such as TiO$_2$, is incorporated into the active phase by solution or solid mixing and precipitation procedures, or vacuum radio frequency sputtering procedures to form a thin film of the pyrochlore oxide on a suitable support. The procedure of Example 5 of the aforesaid 4,129,525 is an example of a suitable procedure for preparing a catalyst for use in the present invention, in this case, a bismuth-rich pyrochlore. The procedure can be modified by providing bubbled oxygen, as in other examples of the patent, or oxygen atmosphere during the formation of the pyrochlore. Oxygen generally accelerates the formation of the pyrochlore.

The process of the present invention can be carried out in general by any procedures suitable for effecting chemical reactions which involve a liquid phase. However, as the reaction involves oxygen, which is generally provided under pressure, it is generally desirable to use reactors capable of use under pressure, such as autoclaves. Basic media are particularly suitable, and aqueous media containing hydroxide ions are preferred. Aqueous alkali solutions are usually employed herein and the counterion to the hydroxide appears to have little effect on results. Thus the cation can be varied widely, but for convenience will usually be chosen from cations which are solubilized in water, such as alkali metals, e.g. Li$^+$, Na$^+$, K$^+$, Rb$^+$, Cs$^+$, quaternary ammonium ions, quaternary phosphorus ions, sulfonium ions, etc. Multi-charged cations containing two or more N, P or S atoms can also be used. Various buffers can also be employed, such as buffer salts or other buffer compounds, to maintain desired pH ranges. In general it will be desirable to use alkaline conditions, such as pH over 7, and it may often be advantageous to use strongly basic conditions such as pH of 12 or more, or even about 14 or nominally higher pH's. The organic compound to be oxidized will be present in the liquid medium and, if soluble, a solute in the solution. If the organic compound is insoluble, it can be present as a phase which is immiscible, in whole or part, with the liquid medium.

The pyrochlore materials utilized are solids which will generally be insoluble in the reaction medium. A number of methods of operation are possible to effect contact of the liquid medium with the solid catalyst in practicing the invention. Thus the pyrochlores can be slurried as a powder in the medium, typically using the material in a size smaller than 325 mesh. (125 meshes/cm, 0.044 mm opening). It is desirable to use good stirring when this method is employed as in a well-agitated autoclave. The organic reactant may be charged as a pure gas, pure liquid, solution or slurry. At times it may be desirable to charge the reactant at a rate to match its rate of oxidation. The concentration of the hydroxide compound may also be controlled, and it may be charged with the reactant, or separately. The reaction can be conducted at ambient pressure, but is generally facilitated by the use of elevated oxygen pressures, with pressures in the range of about 25 to about 100 psi (about 172.4 to about 689.5 kPa) gauge being conveniently employed. In the present process it is not necessary to employ extremely high temperatures, as mildly elevated temperatures, are generally sufficient, and even ambient or lower temperatures are often suitable. Temperatures in the range of above 0° to about 200° C. or higher can be employed, but temperatures in the range of about 20° to about 60° or 100° C. will be preferable for many reactions. For some particular types of reactions, temperatures above 100° C. and possibly up to about 200° C., may be desirable.

In another type of procedure, the organic reactant in liquid medium is passed through or over a mass or bed of pyrochlore solids. Thus the pyrochlore solids can be agglomerated into particles of suitable size and packed into a tube or other usually cylindrical vessel with inlet and outlet, and the liquid medium can be passed through the vessel, along with a stream of oxygen under pressure. Such apparatus can be referred to as a trickle bed, in which the liquid medium containing the organic reactant is allowed to trickle through the bed containing the pyrochlore material. If desired, the pyrochlore material can be employed as active material on a suitable support, with the support being any material on a suitable for use as a catalyst support. Ordinarily such supports are relatively inert siliceous or other mineral materials, or metal oxides, and such materials can be used in the present invention. The supported pyrochlore materials can be used in autoclave or other stirred reactors, as well as in trickle bed procedures. The trickle bed procedure has advantages in some cases in having a higher effective concentration of catalyst with respect to the liquid contacting the catalyst. This appears to aid selectivity to a desired end product in reactions involving some intermediate oxidation products, apparently lessening the tendency to produce undesired side-product.

Reactions which are considered suitable for carrying out employing pyrochlore catalysts, as taught herein, are exemplified by the following reactions:

(1) Primary alcohols to carboxylic acids.

RCH$_2$OH →RCO$_2$H (2) Secondary alcohols to ketones or carboxylic acids.

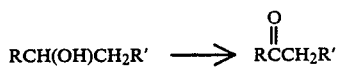

RCH(OH)CH$_2$R'→RCO$_2$H+HO$_2$CR'

(3) Ketones to carboxylic acids.

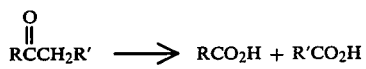

(4) 1,2-Diols, α Ketols, and 1,2 Diones to two carboxylic acids as in (3).

(5) Olefins to two carboxylic acids.

RCH=CHR'→RCO$_2$H+R'CO$_2$H (In the event the olefin is propylene, the second acid will be formic and/or carbonic)

(6) Alkynes to α-diketones or dicarboxylic acids.

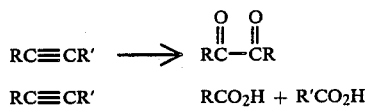

RC≡CR'     RCO$_2$H + R'CO$_2$H (7) Epoxides to carboxylic acids.

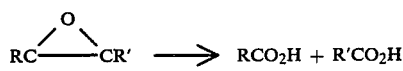

(if R' is H, HCO$_2$H or CO$_3^{2-}$ form)

(8) Aldehydes to carboxylic acids

RCHO→RCO$_2$H (9) Amines to amine oxides

RR'R"N→RR'R"N—O

Cyclic, including heterocyclic, amines can be oxidized, e.g.:

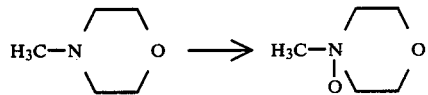

(10) Thioethers to Sulfoxides and Sulfones.

(11) Phosphines to phosphine oxides; phosphites to phosphates

RR'RP"  RR'R"P=O (RO)(R'O)(R"O)P→(RO)(R'O)(R"O)P=O

In the above illustrated reactions (1) through (11), various other groups can be present in the molecule, along with the illustrated functional group, so long as such groups do not unduly interfere with the desired reaction. While the illustrations show the usual case in which the R and R' groups are unchanged, some useful reactions will involve more than one reactive site and production of functional groups or other changes in addition to those illustrated. In the illustrated reactions R, R' and R" can vary widely and can gene;.ally be such groups as alkyl and aryl groups, or such groups including hetero atoms such as N, S and P. The alkyl groups may be cycloalkyl groups. While lower alkyl and phenyl or substituted phenyl groups will be of definite interest, various other groups will also be of interest, with the particular choice of reactants often being determined by the type of product desired and potential reactant sources. In the illustrated reactions, R, R' and R" can also be hydrogen and the reaction will still occur; however, the moieties in which the group is hydrogen will generally be oxidized to formaldehyde, carbonic acid, carbonate ion or some other fundamental compound or the like and this may not produce desirable products. Thus it is generally desirable that at least one of R, R' and R" be some organic group rather than hydrogen. The present invention is generally concerned with processes in which the organic reactant is "partially oxidized" in the sense that it is not completely oxidized to carbon dioxide, i.e. it is desired to oxidize an organic reactant to a recognizable derivative. However, the oxidation may involve different stages or degrees of oxidation. Thus a primary alcohol may be oxidized to an aldehyde and then to a carboxylic acid. In the case of amines, some amines will be oxidized to amine oxides, while others, with more labile substituents, may undergo cleavage, as in the case of a tertiary amine being converted to a secondary amine.

In a particular aspect of the present invention, the pyrochlorate catalysts have been found very suitable for use in oxidizing carbohydrates to polycarboxylated carbohydrates, in a reaction which can be carried out at mild temperatures in liquid medium with molecular oxygen as the oxidizing agent. The reactions involved can be illustrated:

Reaction of Sucrose: (or intermediate levels of oxidation)

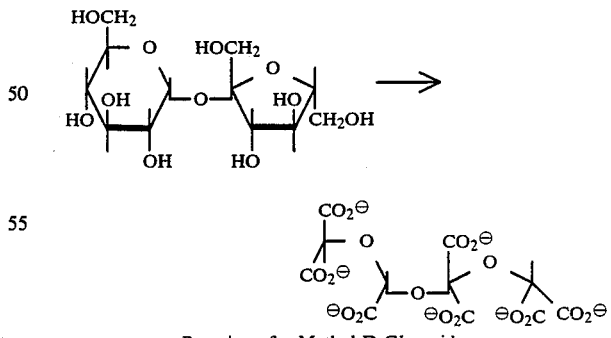

Reaction of α-Methyl-D-Glucoside:

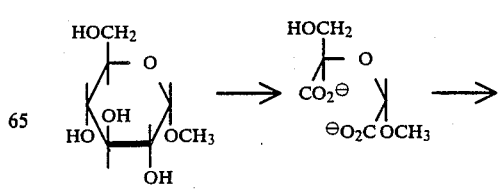

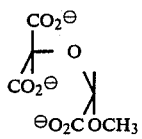

The pyrochlore catalysts can be utilized in the oxidation of various other carbohydrates, such as starches, lactose, etc.

It is an important characteristic of the present catalysts that they are capable of oxidizing both primary hydroxyl, and secondary hydroxyl, as well as of cleaving carbon bonds. The cleaving of vicinal diols, generally to form two carboxylic acid groups, is of particular interest, specially with regard to such structures in carbohydrates, but also in glycols in general with adjacent hydroxyl groups.

In the various reactions illustrated herein, it is to be recognized in the carboxyl or other illustrated acid groups, the cation can be hydrogen ion, or various alkali metal or other metal cations, depending upon the on the counterions present during reaction or utilized in isolation of the product. In general the various acid and salt forms can be readily converted from one to others. Carboxy-containing derivatives of starch have been reported to be useful as detergent builders, see U.S. Pat. No. 3,629,121. Other catalysts for oxidizing carbohydrates have been reported in U.S. Pat. No. 3,860,642 and 3,873,614.

EXAMPLE 1

A 300 ml autoclave was charged with approximately 6 grams of trans-1,2-cyclohexanediol in 100 grams of aqueous 1.5NaOH solution and 4 grams of a finer than 325 mesh 125 meshes/cm) pyrochlore, $Pb_{2.67}Ru_{1.33}O_{6.5}$, which had been prepared by solution precipitation and crystallization. The autoclave was pressurized to 98.5 psi (679.3 kPa) gauge with oxygen, while stirring at 1500 rpm. The temperature was maintained at 25° C. during a 7-hour period. The reaction consumed oxygen, as shown by 161 psi (1110.1 kPa) gauge measurement uptake. The reaction mixture was worked up and analysis, as trimethylsilyl ether derivatives, showed 100% conversion of the cyclohexanediol, with 71.7% selectivity to adipic acid.

EXAMPLE 2

A reactor tube was packed with a bed of particles of the pyrochlore used in Example 1. The pyrochlore, as 40–60 mesh (15–24 meshes/cm, 0.42–0.250 mm openings) particles, was loaded into a 3.2 mm internal diameter reactor tube to form about a 30 cm length packet bed. Calcined silica beads, 0.10 mm diameter, were loaded in front of and following the pyrochlore particles. A 3 to 6 wt% concentration of trans-1,2cyclohexanediol in 1.5 NaOH was pumped through the tube at 25° C., 100 psi (689.5 kPa) gauge $O_2$ at a rate of 5 to 15 cc/hour, with oxygen flow of 20 to 50 cc/minute. The process was continued over a five-day period, with analysis of effluent by gas chromatographic methods showing 100% conversion of the trans-diol substrate with 80–92% selectivity to adipic acid.

EXAMPLE 3

Cyclohexanone was dispersed in aqueous 1.5 NaOH in a 5.36 gram/100 ml concentration, and charged to a 300 ml autoclave along with 4 grams $Pb_{2.62}Ru_{1.38}O_{6.5}$. The reactor was pressurized to 100 psi (689.5 kPa) gauge with oxygen and stirred vigorously. Over an 85 minute period oxygen was consumed, 146 psi (1006.7 kPa) gauge being added to maintain pressure. The temperature increased from 23° to 40° C. Analysis showed a yield of 69% adipic acid with minor amounts of glutaric (3%) and succinic (19%) acids.

Oxidations of trans-1,2-cyclohexanediol were conducted with various noble metal pyrochlore catalysts. A 300 ml autoclave was operated with stirring at 1500 revolutions per minute, employing an aqueous medium containing 100 ml water and other components and conditions as reported in Table 1, with the results obtained. Runs 1 to 6 in the table were conducted at 30 psi (206.9 kPa) gauge oxygen while runs 7 to 12 were conducted at 100 psi (689.5 kPa) gauge oxygen the pH of the reaction medium was generally over 13, both initially and at the end of the reaction, except in run No. 3 where it was slightly below 5 initially and over 5 at the end. Trans-1,2-cyclohexanediol, because of its trans geometry, was employed as model for naturally occurring carbohydrates because the oxidation products were more suitable for routine analysis than those of carbohydrates such as starch. The results demonstrate that the catalysts are effective as oxidation catalysts under mild conditions to convert the cyclohexanediol to adipic acid. While results varied, selectivities to adipic acid as high as 75% were obtained with good conversion. Lower temperatures were found to favor higher selectivity in this reactor, although a higher temperature (55° C.) gave high selectivity when the amount of cyclohexanediol was lowered in Run 5. The apparent strong effect of added alkali indicates that hydroxyl ions are important in the system. In addition to the indicated differences in catalyst components, there were in some cases other variations in form, as for example the bismuth ruthenate catalyst in Run 2 was not a well-developed crystalline form as found in the higher bismuth to ruthenium ratio catalyst in Run 8 which gave over 99% selectivity to adipic acid.

Runs 9 and 10 show that when the active Pb-Ru pyrochlore phase is dispersed on an inert support such as $TiO_2$ or $ZrO_2$, the resulting catalyst has activity, but less activity than pure bulk oxide catalyst.

TABLE 1

Trans-1,2-Cyclohexanediol (TCD) Oxidations to Adipic Acid (AA)

| Run Number | Catalyst Description | SA m²/g | Amount | Initial Moles TCD | Base | T,°C. | Time (min) | Conversion,% | Select.,% |
|---|---|---|---|---|---|---|---|---|---|
| 1 | $Pb_{2.81}Ru_{1.19}O_{6.5}$ | 38.1 | 2.00 g | 0.0517 | 0.300 | 55 | 240 | 97.0 | 22.0 |
| 2 | $Bi_2Ru_2O_7$ | 22.6 | 1.00 g | 0.0517 | 0.114 | 55 | 240 | 45.6 | 6.7 |
| 3 | $Pb_{2.67}Ru_{1.33}O_{6.5}$ | 44.8 | 2.00 g | 0.0517 | None | 55 | 240 | 0.0 | 0.0 |
| 4 | $Pb_{2.67}Ru_{1.33}O_{6.5}$ | 44.8 | 2.00 g | 0.0517 | 0.300 | 25 | 240 | 9.6 | >100.00 |
| 5 | $Pb_{2.67}Ru_{1.33}O_{6.5}$[a] | 44.8 | 2.00 g | 0.0086 | 0.100 | 55 | 240 | 100.0 | 75.00 |
| 6 | $Pb_{2.67}Ru_{1.33}O_{6.5}$ |  | 2.00 g | 0.0517 | 0.300 | 45 | 240 | 97.8 | 31.25 |
| 7 | $Pb_{2.62}Ru_{1.38}O_{6.5}$ | 60.2 | 4.00 g | 0.0517[b] | 0.150 | 25 | 240 | 98.5 | 74.6 |
| 8 | $Bi_{2.46}Ru_{1.54}O_{7-y}$ | 165.3 | 4.00 g | 0.0517 | 0.150 | 40 | 380 | 70.0 | 99.6 |

TABLE 1-continued

Trans-1,2-Cyclohexanediol (TCD) Oxidations to Adipic Acid (AA)

| Run Number | Catalyst Description | SA m²/g | Amount | Initial Moles TCD | Base | T,°C. | Time (min) | Conversion,% | Select.,% |
|---|---|---|---|---|---|---|---|---|---|
| 9 | *Pb$_{2+x}$Ru$_{2+x}$O$_{6.5}$/TiO$_2$ | 66.9 | 4.00 g | 0.0517 | 0.150 | 47 | 90 | 6.7 | 34.0 |
| 10 | **Pb$_{2+x}$Ru$_{2-x}$O$_{6.5}$/ZrO$_2$ | 249.2 | 4.50 g | 0.0517 | 0.150 | 53 | 431 | 14.2 | 4.3 |
| 11 | Pb$_{2.00}$Ru$_{2.00}$O$_{6.5}$ | 0.11 | 4.00 g | 0.0517 | 0.150 | 35 | 60 | 11.0 | 0 |
| 12 | Pb$_{1.15}$Bi$_{1.25}$Ru$_{2.00}$O$_{7-y}$ | 134.0 | 4.00 g | 0.0517 | 0.150 | 55 | 320 | 98.8 | 76.8 |

(a) Part of catalyst recycled from previous runs
(b) Run was made with cis-cyclohexanediol
* 25% of Pb$_{2+x}$Ru$_{2-x}$O$_{6.5}$TiO$_2$
** 33% of Pb$_{2+x}$Ru$_{2-x}$O$_{6.5}$TiO$_2$ A number of oxidations were carried out in a trickle bed, generally as described in Example 2, with representative runs reported in Table 2. In the first four runs the bed was about 30 cm in length and it was about 24 the other runs. The reactions were run under 100 psi (689.5 kPa) gauge oxygen. As shown by the results, high conversions and selectivity to adipic acid were feasible in this method of operation. Adipic acid was the product with each of the substrates employed.

TABLE 2

Oxidation in a Trickle Bed of Trans-1,2-Cyclohexanediol (TCD) ans 1,6 Hexanediol (HD)

| Run | Catalyst | Amount | NaOH | Water | Substrate | Amt. | Rate | O$_2$ Rate | Temp. | Time | Conv.,% | Selec.,% |
|---|---|---|---|---|---|---|---|---|---|---|---|---|
| 1 | Pb$_{2.67}$Ru$_{1.37}$O$_{6.5}$ | 4.69 g | 12 g | 200 ml | TCD | 6 g | 5 cc/hr | 45 cc/min | 26° | 2.5 hr | 100 | 80.9 |
| 2 | Pb$_{2.67}$Ru$_{1.37}$O$_{6.5}$ | " | " | " | " | " | " | " | " | 17 hr | 100 | 90.7 |
| 3 | Pb$_{2.67}$Ru$_{1.37}$O$_{6.5}$ | " | 18 g | 300 ml | " | 18 | " | " | " | 23 hr | 100 | 83.5 |
| 4 | Pb$_{2.67}$Ru$_{1.37}$O$_{6.5}$ | " | 6 g | 100 | TCD | 6 | 15 cc/hr | " | " | 48.5 hr | 99.2 | 82.1 |
| 5 | Pb$_{2.56}$Ru$_{1.44}$O$_{6.5}$ | 4.1 g | 21 | 350 | HD | 21 | 5 cc/hr | 30 cc/min | 55° | 23 hr | 100 | 57.2 |
| 6 | Pb$_{2.56}$Ru$_{1.44}$O$_{6.5}$ | " | " | " | " | " | 2 cc/hr | " | " | 31.4 hr | 100 | 96.5 |
| 7 | Pb$_{2.56}$Ru$_{1.44}$O$_{6.5}$ | " | " | " | " | " | " | " | " | " | " | 84.2 |
| 8 | Bi$_{2.45}$Ru$_{1.55}$O$_{7-y}$ | 3.6 g | 21 | 350 | TCD | 21 | 7.5 cc/hr | 30 cc.min | 45° | 25.4 hr | 100 | 90.4 |

EXAMPLE 4

A reactor tube was packed as described in Example 2, to have 40-60 mesh (15 to 24 meshes/cm) aggregates of catalyst to form a packed bed approximately 24 cm in length containing 2.55 grams catalyst. The catalyst was Bi$_{2.30}$Ru$_{1.70}$O$_{7-y}$. A solution containing 0.127 M maleic acid in 0.67 N aqueous CsOH was pumped over the catalyst at rates varying from 5 to 25 cc/hour with oxygen at 30 cc/minute at 100 psi (689.5 kPa) gauge. The maleic acid, in the form of its cesium salt, was converted to the corresponding oxalate salt, with results as reported in Table 3.

TABLE 3

| Run | T,°C. | Substrate Flow, cc/hr | Conv.(%) | Se.(%) |
|---|---|---|---|---|
| 1 | 95 | 25 | 41.0 | 70.2 |
| 2 | 95 | 15 | 56.0 | 56.0 |
| 3 | 95 | 5 | 97.7 | 53.9 |
| 4 | 95 | 5 | 100. | 58.3 |

CsOH is convenient for use in the above procedure, as cesium oxalate has good solubility in aqueous media, and problems from oxalate precipitation in the catalyst bed are substantially avoided.

EXAMPLE 5

A trickle bed reactor tube was loaded as described in Example 2 with 3.27 9 of 40-60 mesh (15-24 meshes/cm) particles of a Bi$_{2.86}$Ru$_{1.14}$O$_{7-y}$ catalyst having a surface area (BET) of 128.0 m²/g. A solution containing 0.81M 2-butanol in saturated (25° C.) buffer (pH 9.35) was pumped over the catalyst at 3 to 10 cc/hr. under 95-96 psi (655.1 to 662 kPa) gauge, O$_2$ pressure while O$_2$ was fed along with the substrate solution at 30 cc.min. Samples were collected and analyzed using $^{13}$C NMR spectroscopy.

FIG. 1 clearly shows that the initial 2-butanol substrate (tracing A, C-13 resonances at 9.4, 21.6, 31.0, and 69.6 ppm) is converted in part to 2-butanone (tracing B, C-13 resonances for unconverted 2-butanol are at 9.5, 21.7, 31.1 and 69.7, while new resonances due to the 2-butanone product appear at 7.5, 29.1, 36.8 and 218.0 ppm) at 95° C. and 3cc/hr. substrate flow. The identity of 2-butanone is confirmed by comparison with tracing D (C-13 resonances found at 7.8, 29.4, 37.2 and 218.5 ppm) which represents the $^{13}$C NMR spectrum of 0.42M 2-butanone in saturated Na$_2$B$_4$O$_7$ aqueous solution. Tracing C (2-butanol $^{13}$C resonances appear at 9.8, 22.0, 31.4 and 70.0 ppm while 2-butanone $^{13}$C resonances can be seen at 7.8, 29.4, 37.2 and 218.3 ppm) in FIG. 1 shows the $^{13}$C NMR of a sample collected at 115° C. and 10cc/hr. This tracing now shows an additional resonance at 180.9 ppm indicative of a carboxyl group 2-butanol apparently comes from overoxidation of the 2-butanol substrate to give acetate.

The above data indicate that the pyrochlore catalysts are effective for partial oxidation of secondary alcohols to ketones. This also demonstrates that the pyrochlore catalyst can function catalytically in the absence of strong base ([OH$^-$]>1M).

EXAMPLE 6

Oxidized carbohydrates containing carboxylate groups are useful in applications as detergent builders and water-treatment chemicals. An aqueous solution of 0.30 M α-methyl-D-glucoside and 1.26M CsOH was passed over a bed of catalyst particles as described in Example 5. The reaction conditions were 56° C., 95 psi (655.1 kPa) gauge, O$_2$ with an O$_2$ flow rate of 30.0 cc/min, and 10 cc/hr. of substrate. A sample collected from the reactor was analyzed using ion chromatography (IC) with a pulsed amperometric detector (PAD). The PAD consisted of a gold working electrode, glassy carbon counterelectrode, and Ag/AgCl reference electrode. IC analysis of the sample showed 100% conversion of methyl glucoside. Through a combination of IC analyses and $^{13}$C NMR data, the methyl glucoside substrate was found to be converted initially to a mixture of dicarboxylatecontaining products products, $\underline{1}$ to $\underline{3}$ in addition to oxalate and formate by-products.

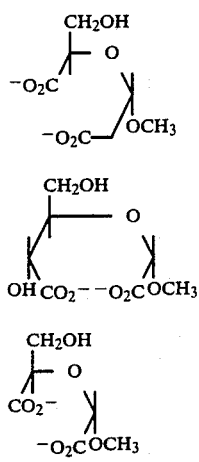

analysis gave 0.113M $\underline{3}$, 0.017M $\underline{2}$ ($\underline{1}$ was not detectable in any of these samples), 0.091M oxalate, and 0.222M formate. This sample was then recycled back over the catalyst (same conditions except 5 cc/hr) to convert more of $\underline{3}$ and $\underline{2}$ to tricarboxylate-containing products $\underline{6}$ and $\underline{5}$, respectively. The tricarboxylate-containing products $\underline{4-6}$ were found to form after oxidation of the primary alcohol group in the corresponding dicarboxylate-containing products $\underline{1-3}$. IC analysis of the recycled

Figure 2:
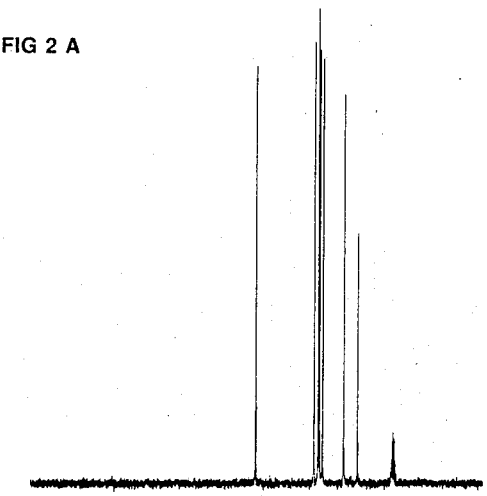
FIG. 2 illustrates NMR spectra of solutions of α-methyl-D-glucoside and oxidation products derived from it.
Figure 2:
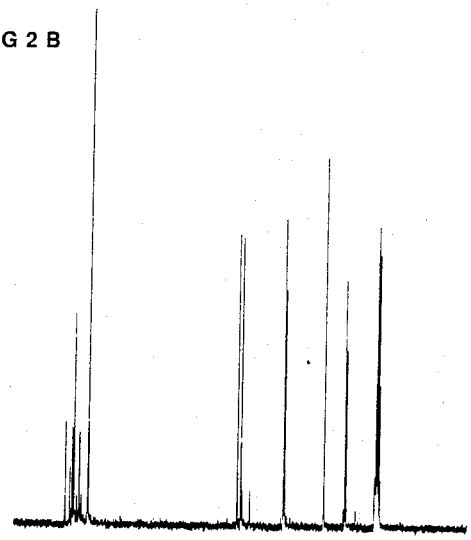
Figure 2:
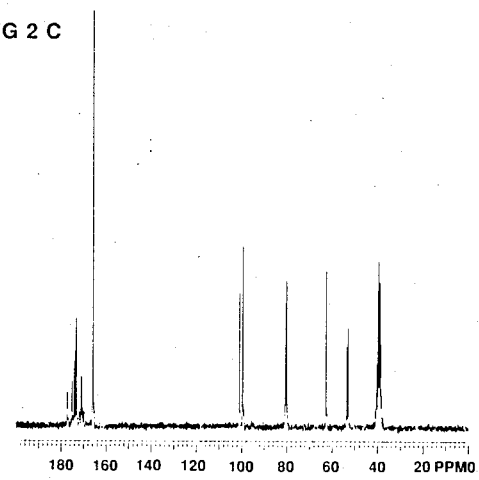

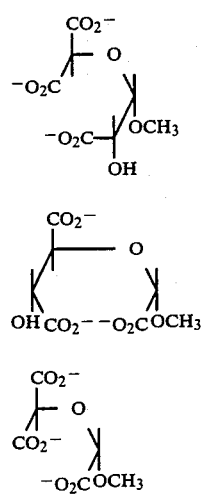

product gave 0.066M 3, 0.004M 2, 0.145M oxalate, and 0.189M formate. Direct IC analysis of 4–6 was not possible using the column and eluent system employed. The 13C NMR spectrum shown in FIG. 2, tracing B, reveals the presence of several carboxyl resonances especially a strong one at 177.3 ppm) in addition to oxalate (174.2 ppm) and formate (173.3 ppm . Tracing A of FIG. 2 provides $^{13}$C NMR spectrum of the starting methyl glucoside substrate. In tracing C the product was recycled once back over the catalyst at 76° C. rather than at 55° C. as in tracing B. The carboxyl resonances in the 160–180 ppm region are indicative of a mixture of oxidized methyl glucoside molecules having the structures shown in $\underline{1-6}$.

EXAMPLE 7

Figure 3:
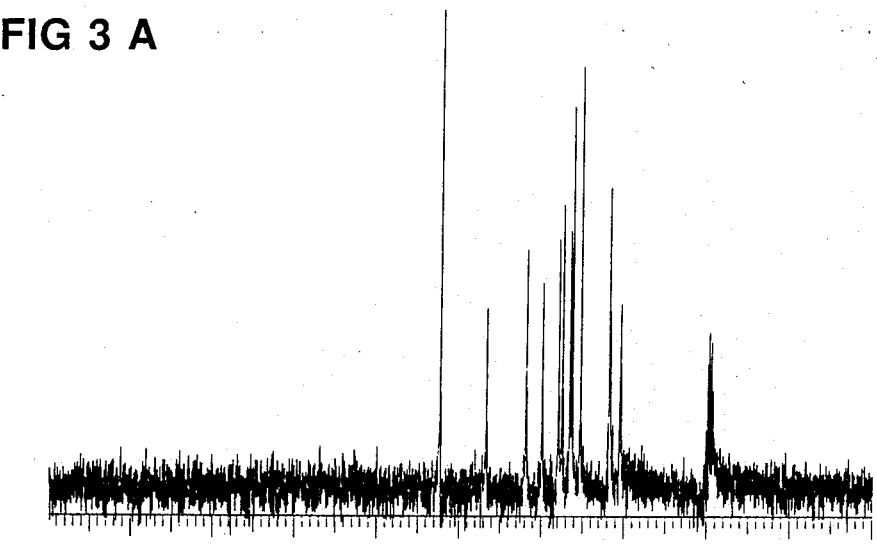
FIG. 3 illustrates NMR spectra of solutions of sucrose and carboxylation products derived from it.
Figure 3:
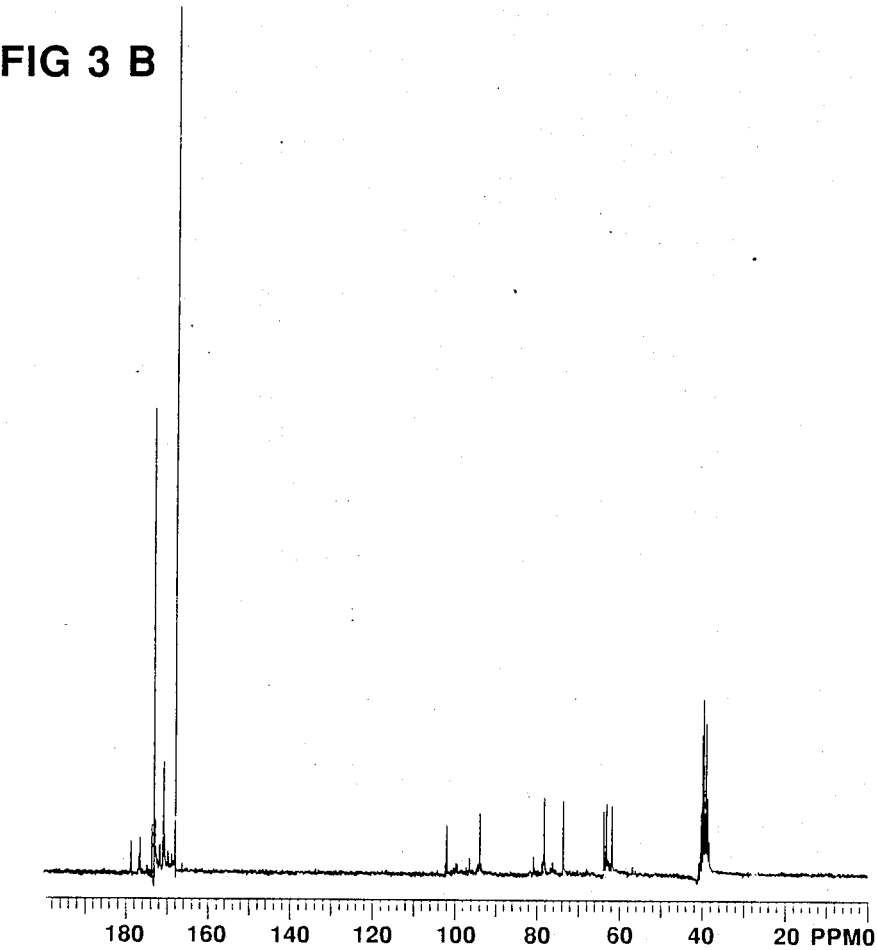

Oxidized products containing carboxyl groups can be obtained by contacting a basic aqueous sucrose solution with the pyrochlorce catalyst described in Example 5. A solution of 0.175M sucrose in 1.60M CsOH was pumped through a reactor at 40° C. containing aggregate particles of $Bi_{2.86}Ru_{1.14}O_{7-y}$. The oxygen pressure was 98 psi 675.81 kPa) gauge, with a flow of 30.1 c/min. The substrate was pumped at a rate of 2 cc/hr. and the product solution collected. Analysis by IC revealed complete conversion of the sucrose substrate had occurred. Formate and oxalate concentrations in the product solution were 0.247 and 0.310 M, respectively, as determined by IC analysis. Additional carboxyl-containing-pieces are present as seen in the $^{13}$C NMR spectrum of the product solution shown in FIG. 3, tracing B. Tracing A of FIG. 3 provides $^{13}$C NMR spectrum of the initial sucrose substrate solution for comparison purposes.

The figures of the drawings are as follows.

FIG. 1-$^{13}$C NMR spectra of 2-butanol in $Na_2B_4O_7$ buffer and various oxidation products derived from it. Spectra include (A) 0.81 M 2-butanol in 25° C.-saturated $Na_2B_4O_7$, (B) mixture of 2-butanol and 2-butanone obtain passing solution in A over a $Bi_{2.86}Ru_{1.14}O_{7-y}$ catalyst at 95° C. and 3 cc/hr. (C) 2-butanol-2-butanone mixture obtained after passing over the same catalyst at 115° C. and 10cc/hr, and (D) authentic sample of 0.42 M 2-butanone in saturated $Na_2B_4O_7$. It is noted that a small carboxyl resonance appears in tracings B and C around 181 ppm as an acetate by-product and that a five-line reference peak for DMSO-d$_6$ appears at 39.5 ppm on all four spectra.

FIG. 2-$^{13}$C NMR spectra of (A) 0.30 M α-methyl-D-glucoside in 1.26 M CsOH, (B) oxidation products after passing the mixture in A over a $Bi_{2.86}Ru_{1.14}O_{7"7}$ catalyst at 56° C. and 10 cc/hr then recycled at 56° C. and 5cc/hr, (C) oxidation products as in B but recycled at 76° C. DMSO-d$_6$ reference peak appears around 39.5 ppm on each spectrum.

FIG. 3-—C NMR spectra of (A) solution of 0.175 M sucrose in 1.60 M CsCH and (B) solution of carboxylated products derived from sucrose after passing over a $Bi_{2.86}Ru_{1.14}O_{7-y}$ catalyst at 40° C. and 2 cc/hr. In both a DMSO-d$_6$ reference quintet appears around 39.5 ppm.

I claim:

1. A method of producing organic compounds which comprises oxidizing alcohols, olefins, alkynes, carbohydrates and carbonyl compounds by contacting said compounds with molecular oxygen in the presence of noble metal pyrochlore compounds represented by $$A_{2+s}B_{2-x}O_{7-y}$$

where A represents pyrochlore structure metal cation, B represents pyrochlore structure metal cation, which is selected from the group consisting of one or more of Ru, Rh, Ir, Os, and Pt, and wherein each of x and y is greater than or equal to zero and less than or equal to 1.0, in the liquid phase, at temperatures up to about 200° C., for a time sufficient to convert said compounds to the organic compounds.

2. The method of claim 1 in which A is Pb or Bi or combinations thereof, and B is Ru.

3. The method of claim 1 in which the liquid phase is aqueous alkaline media.

4. The method of claim 1 in which the pyrochlore is in a form having surface area of at least about 15 meters$^2$/gram.

5. The method of claim 1 in which the oxidation is conducted under elevated pressure.

6. The method of claim 1 in which the oxidation is effected at oxygen pressures in the range of about 25 to about 100 psi (about 172.4 to about 689.5 kPa) gauge.

7. The method of claim 1 in which a carbohydrate is oxidized to a polycarboxylate.

8. The method of claim 1 in which the temperature is no greater than 100 C.

9. The method of claim 1 in which the liquid phase is an aqueous alkaline medium under oxygen pressure and the temperatures are in the range of about 20° C. to about 100° C.

10. The method of claim 1 in which an alcohol is oxidized to an aldehyde, ketone or acid.

11. The method of claim 1 in which an alcohol is oxidized to an acid.

12. The method of claim 1 in which a carboxylic acid is produced.

13. The method of claim 1 in which a vicinal diol is oxidized.

14. The method of claim 1 in which an olefin is oxidized.

* * * * *